United States Patent [19]

Rodler

[11] 4,090,176
[45] May 16, 1978

[54] TELEMETRIC MEASURING APPARATUS FOR BIOLOGICAL OBJECTS

[76] Inventor: Hans Rodler, Pehamweg 3-5, Graz-Neuhart, Austria

[21] Appl. No.: 659,780

[22] Filed: Feb. 20, 1976

[30] Foreign Application Priority Data

Feb. 21, 1975 Austria .................................. 1354/75

[51] Int. Cl.$^2$ ............................................. G08C 19/12
[52] U.S. Cl. ............................ 340/189 M; 340/207 R
[58] Field of Search ..................................... 340/189 M

[56] References Cited

U.S. PATENT DOCUMENTS

| | | | |
|---|---|---|---|
| 2,818,732 | 1/1958 | Bennett | 340/189 M |
| 2,910,683 | 10/1959 | Todd | 340/189 M |
| 3,051,896 | 8/1962 | Bieganski | 340/189 M |
| 3,218,638 | 11/1965 | Honig | 340/189 M |
| 3,253,588 | 5/1966 | Vuilleumier | 340/189 M |
| 3,268,880 | 8/1966 | Miller | 340/189 M |
| 3,299,424 | 1/1967 | Vinding | 340/189 M |
| 3,303,701 | 2/1967 | Matsuura | 340/189 M |
| 3,310,736 | 3/1967 | Bayly | 340/189 M |
| 3,576,554 | 4/1971 | Temps | 340/189 M |
| 3,656,132 | 4/1972 | Brumbelow | 340/189 M |
| 3,713,124 | 1/1973 | Durland | 340/189 M |

Primary Examiner—Thomas B. Habecker
Attorney, Agent, or Firm—Kurt Kelman

[57] ABSTRACT

Signals from a high frequency transmitter outside of the biological object are received in a resonant receiving circuit inside the object whose resonant frequency corresponds to the value of the parameter being measured. The signal from the resonant receiving circuit is applied to the input of a frequency multiplier whose output is connected to a second resonant circuit tuned to the multiplied frequency. The second resonant circuit transmits a return signal to a receiver outside of the biological object which is also tuned to the higher frequency. The signal at the receiver will have a maximum amplitude when the transmitter frequency is equal to the frequency of the first resonant circuit as tuned by the value of the parameter. The adjustment of the transmitter frequency required for receiving maximum energy at the receiver is a measure of the value of the parameter in a first embodiment. An alternate embodiment, the frequency of the transmitter is wobbled by means of a sawtooth voltage generator, the time difference between the sawtooth flyback and the maximum amplitude of the signal at the receiver constituting a measure of the value of the parameter.

14 Claims, 10 Drawing Figures

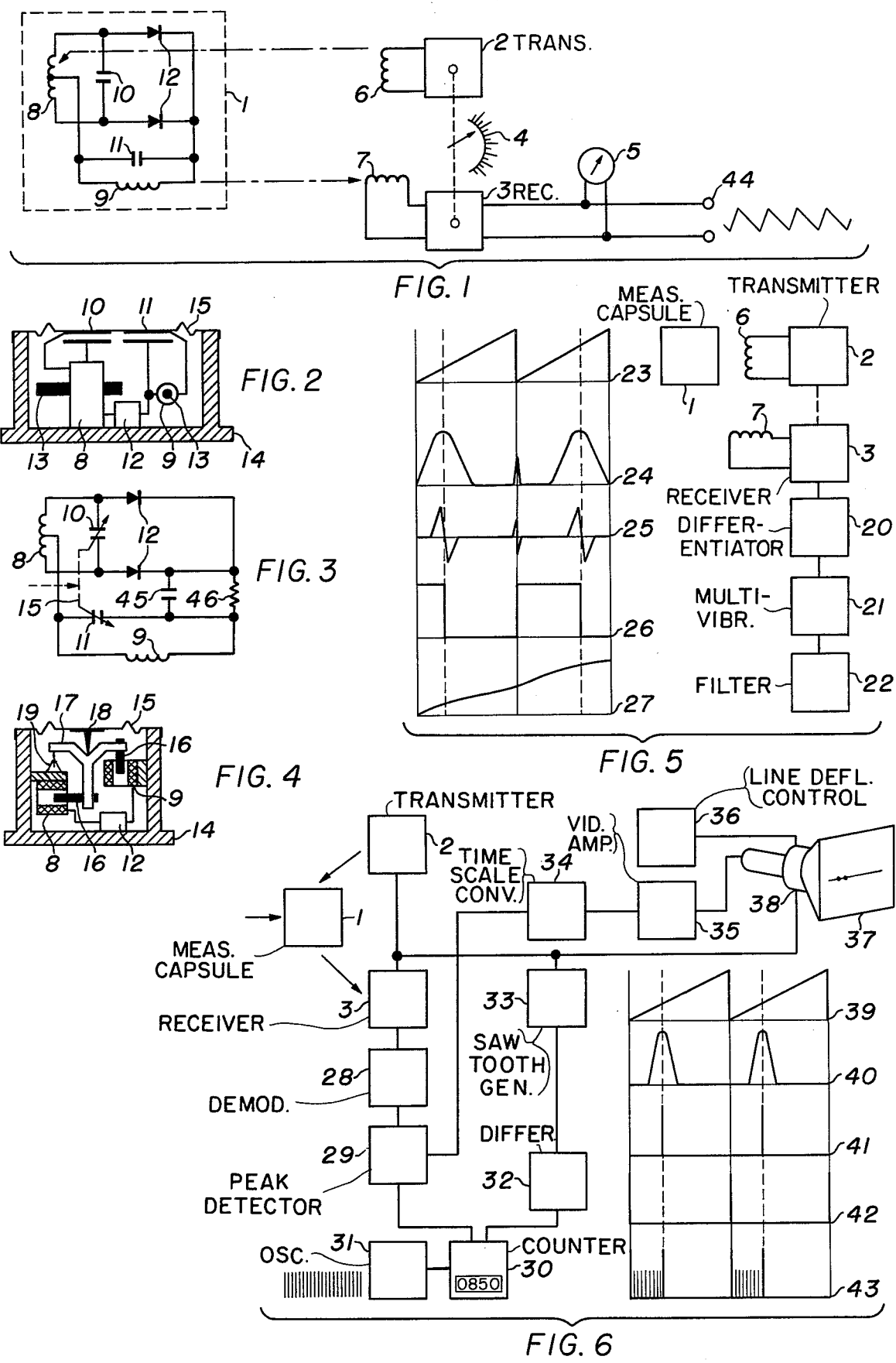

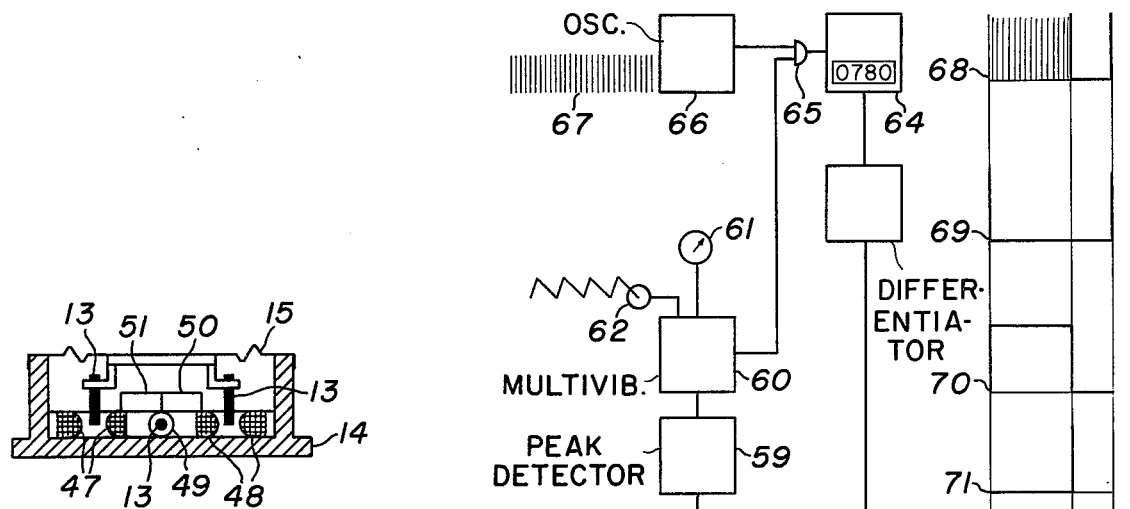
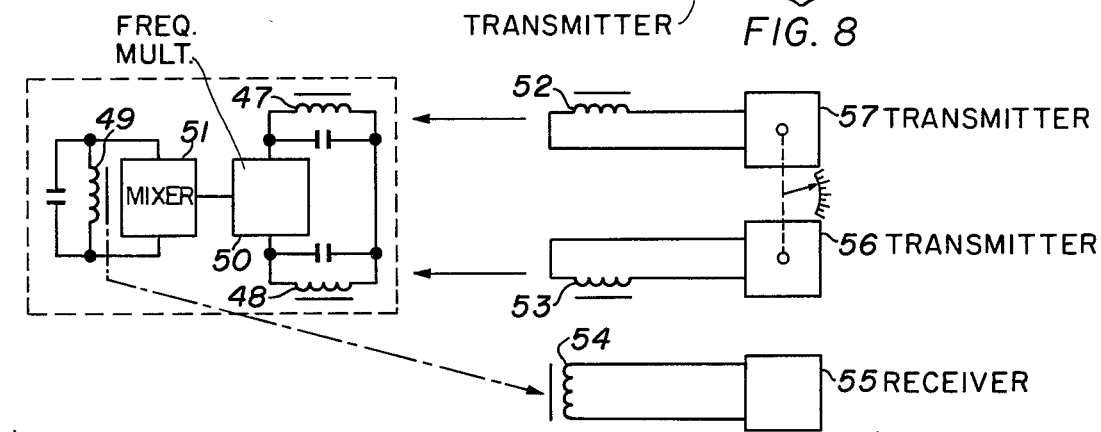
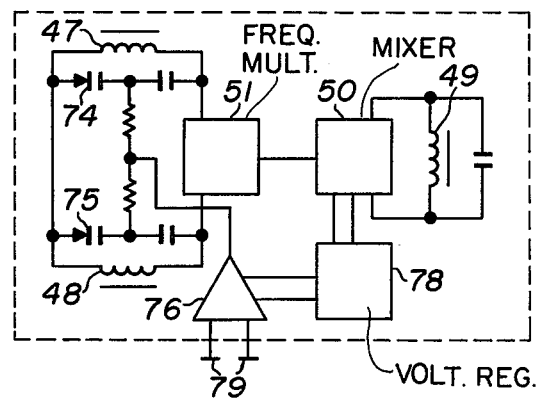

TELEMETRIC MEASURING APPARATUS FOR BIOLOGICAL OBJECTS

The present invention relates to a measuring apparatus for measuring parameters in a biological object In this apparatus a transmitter is located outside of the object and transmits high frequency signals towards the object. Further, a measuring capsule is implanted in the object. The measuring capsule responds to the parameter being measured and modulates the received high frequency signal in correspondence thereto. A receiver located outside of the object receives the so-modulated signals.

In one known apparatus of this general type, the measuring capsule contains a signal transmitter signal and a battery supply current to the transmitter signal. The parameter to be measured modulates this emitter. The receiver includes indicator showing the measured value of the parameters. The operating life of such an apparatus is limited to the life of the battery and the transmitter signal arrangement is relatively complicated. Because of the limited battery life, such an apparatus cannot be used in cases where parameters are to be measured for years while the measuring capsule remains implanted in the object.

In other known apparatus of this type, the frequency of a resonant circuit arranged inside the object varies as a function of the value of the parameter being measured. This resonant frequency is measured externally. The external measuring instrument must be very close to the resonant circuit because measurements are otherwise not possible. Also, the accuracy of this apparatus is low.

It is the primary object of this invention to provide a telemetric measuring apparatus of the indicated type, which makes it possible to take accurate measurements of parameters in a biological object over a long period of time.

It is another object of the invention to provide apparatus for measuring periodic variations in the value of a given parameter and to provide a curve showing these variations as well as the absolute values.

The present inventions provides apparatus for measuring the value of a predetermined parameter in a biological object. It comprises transmitter means located outside of said object for transmitting a transmitter signal having a first frequency towards said biological object. It further comprises first resonant circuit means located inside said object and having a resonant frequency varying as a function of said value of said parameter, for receiving said transmitter signal and modulating same in correspondence to said value of said parameter, thereby furnishing a modulated transmitter signal. It further comprises second resonant circuit means connected to said first resonant circuit means and tuned to a second frequency different from said first frequency, for transmitting a resonant output signal in response to said modulated transmitter signal, the so-transmitted resonant output signal constituting a return signal. Signal receiver means located outside said object are also supplied, for receiving said resonant output signal and furnishing an indication thereof. Finally, output means connected to said transmitter means are provided, for changing the frequency to said transmitter signal until said resonant output signal is a maximum value indicative of correspondence between said transmitter signal frequency and said resonant frequency of said first resonant circuit means. The so-determined transmitter signal frequency constitutes a measure of said value of said parameter.

The above and other objects, advantages and features of this invention will become more apparent from the following detailed description of certain now preferred embodiments thereof, taken in conjunction with the accompanying drawing wherein FIG. 1 is a circuit diagram showing an embodiment of a measuring apparatus which requires manual transmitter and receiver adjustment;

FIG. 2 shows the measuring capsule of FIG. 1, with capacitive adjustment;

FIG. 3 is a basic diagram of modified measuring capsule circuitry;

FIG. 4 shows a measuring capsule with inductive adjustment;

FIG. 5 shows a circuit diagram of an automatic recording device with wobbled transmitter and receiver frequencies;

FIG. 6 shows a circuit diagram of an automatic measuring apparatus furnishing a digital indication and also including analog curve recording apparatus using a Braun tube;

FIG. 7 shows a measuring capsule with two receiver circuits and one transmitting circuit;

FIG. 8 shows an automatic measuring apparatus utilizing two transmitters and one receiver and furnishing a digital indication;

FIG. 9 shows a measuring apparatus utilizing two transmitters having a manual frequency adjustment and one fixed frequency receiver; and FIG. 10 shows a measuring capsule for other parameters.

FIG. 1 shows a measuring capsule 1 which is implanted in a biological object (not shown), a high frequency transmitter 2 and a receiver 3, both located externally of the object. The transmitter and receiver are mechanically coupled to each other. Manual adjustment device 4 (one embodiment of output means) for the transmitter and receiver is calibrated in units of the values to be measured. Galvanometer 5 is connected to the output of receiver 3 to indicate the maximum value.

The first resonant circuit means includes an antenna 8 which also constitutes the inductance of the resonant circuit and a capacity 10 connected in parallel thereto, either the inductance or the capacity of the circuit changing in accordance with changes in the parameter being measured. Frequency multiplier 12 is connected between the resonant receiver circuit (first resonant circuit means) and transmitter circuit 9, which is also constituted by an inductive antenna, and a capacity 11 connected in parallel thereto, either the inductance or the capacity of the transmitter circuit changing in accordance with changes in the parameter being measured. Transmitting circuit 9 is herein referred to as second resonant circuit means. The frequency multiplier is a full-wave rectifier circuit which effectively doubles the frequency.

External transmitter 2 includes transmitter antenna 6 and external receiver 3 includes receiver antenna 7. Receiver 3 will receive the maximum energy when emitter antenna 6 and receiver antenna 8, transmitting antenna 9 and outside receiver antenna 7 are in resonance. When the measured parameters from the object change the resonance points of antennas 8 and 9, antennas 6 and 7 must be adjusted to the same value. Thus, the manual adjustment device 4 directly indicates the value of the parameter being measured.

If transmitter 2 and receiver 3 are tuned to the rising component of the resonance curve, periodic changes in the value of the parameter may be recorded by a stylo recorder connected at 44 to the output of the external receiver, adjustment of device 4 simultaneously recording calibrating comparison values.

FIG. 2 shows a vertical section of measuring capsule 1, wherein the resonant circuits are capacitatively tuned. The measuring capsule is designed to measure pressures and includes housing 14 closed by pressure-responsive membrane 15. The membrane together with a suitable electrode forms capacities 10 and 11.

Antennas 8 and 9 are ferrite antennas comprising coils receiving ferrite cores 13. The antennas form resonant circuits with capacities 10 and 11. Diode 12, which is connected between the resonant circuits causes the frequency in transmitter circuit 9 to be double that of receiver circuit 8. When membrane 15 is subject to pressure, the distance between the electrodes of the capacities is reduced correspondingly, thereby changes the resonant frequency in the transmitter and receiver circuits.

As shown in FIGS. 1 and 2, antennas 8 and 9, as well as antennas 6 and 7 are arranged perpendicularly to each other so that transmitter and receiver are decoupled and do not influence each other. While a full-wave rectifier has been shown as frequency multiplier means to double the frequency and this arrangement is very effective, other frequency multipliers are well known and may be used herein.

In the basic circuit diagram of FIG. 3, the same reference numerals designate the same parts as in FIGS. 2 and 1. A condenser 45 is connected between rectifier 12 and capacity 11 and resistance 46 is connected between the antennas, for matching the transmitting circuit to the receiver circuit whereby an improved figure of merit of the two circuits is obtained.

FIG. 4 is a section showing a measuring capsule circuit with inductive tuning. The same reference numerals again designates the same parts. In this embodiment, the capacities of the resonant circuits are fixed. Ferrite cores 16 of the resonant circuits are affixed to respective arms of beam 17 which is positioned by spring 19 and moved by membrane 15 and rod 18 which is attached thereto and engages the beam. Upon a change in the pressure acting on membrane 15, rod 18 will move beam 17 against the action of spring 19 to cause the ferrite cores to move in relation to their surrounding cores, thus changing the resonant frequency of circuits 8 and 9.

FIG. 5 shows a circuit diagram of an automatic measuring apparatus with measuring capsule 1, external signal transmitter 2 and external signal receiver 3. In this embodiment, sawtooth oscillator signal 23 is applied to transmitter 2 and receiver 3 for wobbling the transmitter and receiver resonant frequencies. This causes the signal received by external receiver 3 to vary in accordance with curve 24. The peak of curve 24 depends solely on the resonant frequency in the circuits in the measuring capsule. The received signal is differentiated by a differentiator 20, the output of which is shown as curve 25. The negative part of this signal is used to toggle a bistable multivibrator 21. The multivibrator is also toggled by the flyback portion of the sawtooth wave, the latter being shown as a narrow pulse in the center of curve 25. This produces pulse 26 whose width depends on the position of the resonance point. A low-pass filter 22 is connected to multivibrator 21 to convert pulse-width modulated curve 26 in a known manner to analog curve 27. In other words, this arrangement provides pulse width modulation converted by a low-pass filter into an analog signal having an amplitude varying in correspondence to the measured parameter and which may be displayed or recorded.

In the circuit arrangement of FIG. 6, saw-tooth generator 33 is again arranged to wobble the signals of outside transmitter 2 and, if desired, outside receiver 3. The saw-tooth shaped frequency variation 39 of the high frequency signal transmitted by transmitter 2 produces resonance curve 40 in receiver 3 after demodulation by circuit 28. A peak detector including pulse former 29, which is connected to demodulator stage 28, produces a narrow pulse from resonance signal 40. Simultaneously, further differentiating circuit 32 produces pulse 42 from the flyback of the saw-tooth signal. This pulse produces a reset to zero and starts digital counter 30 which counts pulses from oscillator 31. Pulse 41 produced by generator 29 stops the counter. The counted pulses of oscillator 31 correspond exactly to the interval between the starting pulse and the maximum valve of the resonance curve, and thus indicate directly the digital values of the parameters acting on the circuits in measuring capsule 1. The output of pulse former 29, namely pulse 41, is also applied through a time scale converter 34 and a video amplifier 35 to the cathode of a Braun tube 37. Saw-tooth pulse 39 is triggered by line deflection unit 36 of the Braun tube. Pulse 41 produces a narrow intensity modulation pulse on the cathode of the Braun tube. Since line deflection unit 36 is sychronized to pulse 41, the position of the dark or light spot corresponds to the analog value of the parameter being measured. Time scale converter 34 allows a readily discernible curve to be generated even for slowly varying changes in the parameters, both line (horizontal) and frame (vertical) deflection circuits being operated in a manner conventional in television.

When a sawtooth pulse generator is used as a frequency modulator, the rate of voltage increase can be adjusted to correspond to the rate of change of frequency within the circuits of the measuring capsule. In both FIGS. 5 and 6 the flyback of a sawtooth voltage generator starts the timing curcuit, be it digital or analog. In FIG. 6 the cathode tube deflection is triggered by this flyback signal, thus establishing a direct relationship between the start of the deflection and the production of a light spot on the cathode for periodic variations in the measured value of the parameter, and an analog curve can be obtained, the time scale conversion making it possible to obtain any desired recording speed.

FIG. 7 is a cross section of another measuring capsule embodiment. The capsule again includes housing 14 closed by pressure-responsive membrane 15, the receiving circuit in the capsule including two resonant circuits each consisting of ferrite cores 13 affixed to the membrane and respectively received in coils 47 and 48. The two circuits are tuned to different frequencies. Heterodyne circuit 51 is connected to both resonant circuits and produces a constant intermediate frequency signal. The intermediate frequency is multiplied in unit 50 the transmitter antenna circuit is connected to the frequency multiplier unit and tuned thereto for transmitting the multiplied signal from the capsule. In this embodiment, the parameter to be measured the resonant frequencies of the two receiver circuits 47 and 48 so that a constant intermediate frequency is produced for all measured values. This can be accomplished by changes in either the circuit inductance or capacitance. For this embodiment, the The external transmitter means consist of a first transmitter tuned to one of the resonant circuits and a second transmitter tuned to the other resonant circuit. The mixing of the two frequencies in the capsule and the frequency multiplication may be obtained simply by diode combinations. The transmitter antenna in the capsule and the external receiver may be tuned to a fixed frequency, which produces favorable amplification and separation characteristics in the receiver. If the measuring parameter changes the resonant frequency in the receiver circuits in the capsule, the two outside transmitters, which are coupled to each other, must be tuned until the receiver again receives a maximum energy.

An automated arrangement with two external transmitters 56 and 57 is shown in FIG. 8. The frequency ratio between transmitters 56 and 57 is the same as that between the two receiver resonance circuits in capsule 1 to produce a constant intermediate frequency, as described hereinabove in connection with FIG. 7. Sawtooth voltage generator 58 modulates the frequency of transmitters 56 and 57 by the slowly rising saw-tooth voltage and the modulated signal is received from capsule 1 by external receiver 55. The signal received by external receiver 55 is shown as curve 72. The peak of this curve is detected by peak detector 59, which generates pulse 71. Pulse 71 and the flyback of the sawtooth generator again determine the pulse width of a pulse width modulated pulse 70. This pulse is applied to one input of an AND gate 65 whose other input receives counting signals generated by an oscillator 66. The counting signals are shown in curve 68. An analog indicator 61 as well as a stylo recorder 62 are connected to the output of bistable multivibrator 60.

Periodic variations in the value of the parameter being measured may thus be indicated and recorded. It is the particular advantage of this arrangement that only the transmitter frequencies need be changed. The receiver is tuned to a constant frequency.

Periodic changes in the value of the parameter being measured and corresponding changes in the resonant frequency in the receiver circuit in the capsule cause the external transmitter means and the capsule receiver means to be rhythmically out of phase whereby the voltage received in the external receiver is modulated in accordance with changes in the parameter. This change in amplitude may, after demodulation, be fed directly to a recording instrument. After the resonant circuit of the external transmitter and receiver means has been tuned to the resonant frequency of the capsule circuit, the frequency constitutes a measurement for the absolute value of the parameter. Thus, the absolute value of the parameter is solely a function of the frequency and the distance between the measuring capsule and the external receiver and transmitter does not influence the measuring results. A recorded curve of periodically varying parameters is best produced from the decreasing component of the resonance curve, a comparison of the absolute values between maxima and minima resulting from the frequency shift at the external transmitter and receiver producing another measurement of the absolute values independent of the distance between capsule and external receiver and transmitter.

FIG. 9 shows such an arrangement for manual adjustment or tuning of external transmitters 56 and 57 whose frequency difference is the same as that of receivers 47 and 48 in the capsule. The tuning device is calibrated in parameter units and the frequency ratio between oscillators 56 and 57 is such that a constant intermediate frequency is produced in the capsule in accordance with the above description of FIG. 7. The frequencies of transmitters 56 and 57 are transmitted by antennas 52 and 53 and received by resonant circuits 47 and 48. The multiplied frequency is transmitted by resonant circuit 49, and received by antenna 54 of external signal receiver 55.

FIG. 10 shows a circuit diagram of a measuring capsule for measuring electrical parameters, the same reference numerals designating like parts as in FIG. 9. Capacities 74 and 75 in the receiver circuits and diodes controlled by amplifier 76. Voltage stabilizer 78 delivers the operating voltage from the intermediate frequency received from heterodyne circuit 50. Receiving electrodes 79 are mounted on the outside wall of the capsule to sense electrical parameters.

When the capsule has a pressure-responsive membrane controlling the resonant circuits in the capsule, the apparatus may be used to measure pressures on the biological object. The membrane may be metallic to form one electrode of a capacitor having a capacity changed by the change in distance between its two electrodes due to pressure deformation of the membrane. These pressure-responsive capacities and the inductances which also constitute antennas form the resonant circuits of the capsule. On the other hand, if the membrane is connected with a lever system controlling the movement of iron cores in coils, displacement of the membrane under pressure will change the inductivity of the circuit.

Such a pressure-responsive measuring capsule may be implanted into the brain of a patient after a tumor operation, for instance, so as to indicate growth of a new tumor.

Since such measuring capsules do not require their own energy source, they may be left implanted in the patient for years and may thus be used to monitor pressure conditions inside the patient for very long periods of time.

Such a device may also be used to measure the temperature if a shield is provided over the movable membrane to protect it from outside pressures, since the gaseous pressure applied to the capsule membrane changes linearly with the temperature according to Gay-Lussac's law, $P = (Po/To)T$. Particularly when capacitive resonant tuning is used, the measuring capsule may be filled with a liquid, for instance methyl alcohol, the expansion of the liquid due to a change in the temperature being converted into a change in the capacity and a corresponding change in the resonant frequency.

The measuring apparatus of the present invention comprises only passive elements so that it will not deteriorate with age.

As will be obvious from the above description of certain now preferred embodiments, various parameters in biological objects may be measured with the apparatus, including pressure, temperature, movements, acceleration, changes in the distance between two parts, as well as changes in the electrical resistance of the surrounding tissues. Signals varying as electrical phenomena, such as ion concentrations, ion currents, electrocardiograms and the like, may be amplified by a built-in integrated amplifier and used to change the resonant frequencies in the capsule by pre-magnetizing the ferrite cores of the resonant circuits or controlling capacity diodes. The integrated amplifier is energized by the direct current produced by the frequency multiplier. Alternatively, the amplifier may be energized by the received frequency. In the embodiment of FIG. 10 the electrodes on the surface of the measuring capsule are connected to the input of the amplifier. The amplified signals are used directly to pre-magnetize the ferrite cores or to change the capacity of the capacity diodes connected in parallel thereto. Since the electrical parameters usually change relatively slowly, it is generally sufficient to use a manually tuned external emitter-receiver system whose output has an amplitude demodulation, the external system being tuned one side of the resonance curve of the implanted capsule.

The measuring capsule of the present invention operates with wireless reception and transmission of energy. The measuring parameters change only the resonant frequency of the circuits in the capsules. The frequencies received and transmitted by the capsules are different, thereby minimizing interference between the two signals. A number of advantages are derived from such a structure. During measurements, the apparatus only emits and receives energy. No chemical reactions, such as encountered in battery-operated devices, can occur. The simplicity of the system assures a long operating life and stability. The measuring capsule may be sterilized and the apparatus can be serviced and operated simply. The measuring results are very accurate in recording a measuring curve as well as in measuring absolute values of the parameters.

What is claimed is:

1. Apparatus for measuring the value of a predetermined parameter in a biological object, comprising, in combination, transmitter means located outside of said object for transmitting a transmitter signal having a first frequency toward said biologicl object; first resonant circuit means located inside said object and having a resonant frequency varying from a first frequency as a function of said value of said parameter, for receiving said transmitter signal and modulating the same in correspondence to said value of said parameter, thereby furnishing a modulated transmitter signal; second resonant circuit means connected to said first resonant circuit means and tuned to a second frequency different from said first frequency, for transmitting a resonant output signal in response to said modulated transmitter signal, the so-transmitted resonant output signal constituting a return signal; signal receiver means located outside said object for receiving said resonant output signal and furnishing an indication thereof; and output means connected to said transmitter means for changing the frequency of said transmitter signal until said resonant output signal has a maximum value indicative of correspondence between said transmitter signal frequency and said resonant frequency, the so-determined transmitter signal frequency constituting a measure of said value of said parameter.

2. The apparatus of claim 1, wherein said parameter is the pressure at a predetermined point within said biological object; and wherein said first resonant circuit means includes an inductance having a coil and a core, and pressure-responsive means for moving said core relative to said coil, thereby changing the inductivity of said coil as a function of said pressure.

3. The apparatus of claim 1, wherein said signal receiver means comprises means tuned to a said second frequency, and wherein said resonant circuit means further comprises frequency multiplier means connected to said first and second resonant circuit means for changing the frequency of said modulated transmitter signal by a factor corresponding to the ratio of said second to said first frequencies.

4. The apparatus of claim 3, wherein said second resonant circuit means includes at least one circuit element having an impedance varying in correspondence to variations in said predetermined parameter, the resonant frequency of said second resonant circuit means varying in correspondence to said variations in said impedance of said circuit element; and wherein said output means comprises manual adjustment means connected to said transmitter means and said signal receiver means.

5. The apparatus of claim 3, wherein said parameter is the pressure within said biological object; and wherein said first resonant circuit means includes a membrane constituting at least part of one electrode, and a second electrode opposite said one electrode, said one and second electrodes together constituting a capacitor having a capacity varying as a function of said pressure.

6. The apparatus of claim 3, wherein said parameter is an electrical signal; wherein said first resonant circuit means includes a diode having a capacity varying as a function of voltage applied thereto; and wherein said measuring means further comprise a probe for receiving said electrical signal, an amplifier connected to said probe for amplifying said electrical signal thereby furnishing an amplified electrical signal, and means for connecting said amplifier to said diode, whereby the capacity of said resonant circuit means varies as a function of said electrical signal.

7. The apparatus of claim 3, wherein said first and second resonant circuit means each have an inductance constituting an antenna, and wherein said antennas are arranged at right angles to each other.

8. The apparatus of claim 3, further comprising transmitter frequency modulating means connected to said transmitter means for changing the frequency of said transmitter signal periodically over a predetermined frequency range from said first frequency, whereby said return signal is an amplitude modulated signal having a maximum value when the frequency of said transmitter means is equal to the frequency of said first resonant circuit means; and wherein said output means comprises means for furnishing an output signal indicative of the time difference between the occurrence of said maximum value of said amplitude modulated signal and a predetermined time instant in the operating cycle of said tramsmitter frequency modulating means.

9. The apparatus of claim 8, wherein said means for furnishing an output signal comprises means for furnishing an analog output signal.

10. The apparatus of claim 9, wherein said means for furnishing an analog output signal comprises differentiating circuit means connected to said signal receiver means for differentiating said return signal and furnishing a first differentiator signal at said predetermined time instant and a second diffentiator signal upon occurrence of said peak value, bistable circuit means connected to said differentiating circuit means for furnishing a pulse signal having a pulse width corresponding to the time interval between said first and second differentiator signal, and filtering means connected to said bistable circuit means for furnishing said analog output signal in response to said pulse signal.

11. The apparatus of claim 8, wherein said output signal is a digital output signal.

12. The apparatus of claim 11, wherein said means for furnishing an output signal comprise differentiating circuit means connected to said receiver means for differentiating said return signal and furnishing a first and second differentiator signal in response thereto, a digital counter having a "start" input connected to said differentiating circuit means for receiving said second differentiator signal, a "stop" input connected to said differentiating circuit means for receiving said first differentiator signal, and a counting input, and a counting signal furnishing means for furnishing counting signals to said counting input of said digital counter, whereby the number of counting signals counted by said digital counter from receipt of said "start" to receipt of said "stop" signal constitute a visual indication of said value of said parameter.

13. The apparatus of claim 8, wherein said means for furnishing an output signal comprises a Braun tube having a cathode and a horizontal deflection circuit, means for synchronizing said transmitter frequency modulating means to said horizontal deflection circuit of said Braun tube, pulse former means connected to said signal receiver means for furnishing a pulse when said return signal has said maximum value, and means for applying said pulse to said cathode of said Braun type.

14. The apparatus of claim 8, wherein said transmitter means comprises means for transmitting a first and second high frequency signal having a first and second transmitter frequency respectively; wherein said first resonant circuit means comprise a first and second resonant circuit having a frequency ratio corresponding to the ratio of said first to said second transmitter frequency, heterodyning circuit means connected to said first and second resonant circuits for furnishing an intermediate frequency signal having a constant frequency in response to said first and second high frequency signal; wherein said frequency changing means comprise a frequency multiplier circuit for furnishing a frequency-multiplied intermediate frequency signal; and wherein said second resonant circuit means comprise means for transmitting said frequency-multiplied intermediate frequency signal to said signal receiver means.

* * * * *